(12) United States Patent
Nelson et al.

(10) Patent No.: US 7,494,809 B2
(45) Date of Patent: Feb. 24, 2009

(54) AUTOMATED CELL SAMPLE ENRICHMENT PREPARATION METHOD

(75) Inventors: Alan C. Nelson, Gig Harbor, WA (US); Florence W. Patten, Issaquah, WA (US)

(73) Assignee: VisionGate, Inc., Gig Harbor, WA (US)

( * ) Notice: Subject to any disclaimer, the term of this patent is extended or adjusted under 35 U.S.C. 154(b) by 358 days.

(21) Appl. No.: 11/353,353

(22) Filed: Feb. 14, 2006

(65) Prior Publication Data
US 2006/0183220 A1    Aug. 17, 2006

Related U.S. Application Data

(63) Continuation-in-part of application No. 10/984,221, filed on Nov. 9, 2004, now abandoned.

(51) Int. Cl.
*C12N 5/06* (2006.01)
*C12M 3/00* (2006.01)

(52) U.S. Cl. .............. 435/325; 435/289.1; 210/644; 210/645; 210/649; 210/650; 210/651; 210/767; 210/791; 210/797; 210/798; 210/806

(58) Field of Classification Search ............ 210/644, 210/645, 649, 650, 651, 767, 791, 797, 798, 210/806; 435/325, 289.1
See application file for complete search history.

(56) References Cited

U.S. PATENT DOCUMENTS

| | | | |
|---|---|---|---|
| 3,470,373 | A | 9/1969 | Brewer |
| 3,497,690 | A | 2/1970 | Wheeless, Jr. |
| 3,598,471 | A | 8/1971 | Baldwin |
| 3,657,537 | A | 4/1972 | Wheeless, Jr. |
| 3,748,468 | A | 7/1973 | Hartman |
| 3,833,762 | A | 9/1974 | Gudmundsen |
| 3,960,449 | A | 6/1976 | Carlton |
| 3,999,047 | A | 12/1976 | Green |
| 4,175,860 | A | 11/1979 | Bacus |
| 4,183,623 | A | 1/1980 | Haines |

(Continued)

FOREIGN PATENT DOCUMENTS

WO    WO 02/095476 A2    11/2002

OTHER PUBLICATIONS

Kikuchi, S. et al., "Three-dimensional computed tomography for optical microscopes," Optics Communications 107 (1994) 432-444.

(Continued)

*Primary Examiner*—John Kim
(74) *Attorney, Agent, or Firm*—Citadel Patent Law; George A. Leone; J. A. Claypool (57) ABSTRACT

A method for automated cell enrichment preparation where biological cells are injected into a first subchamber and flowed through the first subchamber, through a large pore filter and into a second subchamber so that the large pore filter retains particles large particles in the first subchamber, while the biological cells pass through the first filter into the second subchamber and are retained by a small pore filter. After clearing, the biological cells are stained. A solvent exchange leaves the biological cells in solvent and they are released into a concentration module where a portion of the solvent is removed to form an enriched concentrated cell suspension.

14 Claims, 7 Drawing Sheets

U.S. PATENT DOCUMENTS

| | | | |
|---|---|---|---|
| 4,200,353 | A | 4/1980 | Hoffman |
| 4,293,221 | A | 10/1981 | Kay |
| 4,360,885 | A | 11/1982 | Edgar |
| 4,755,287 | A | 7/1988 | Jones |
| 4,858,128 | A | 8/1989 | Nowak |
| 4,873,653 | A | 10/1989 | Grosskopf |
| 4,891,829 | A | 1/1990 | Deckman et al. |
| 4,994,213 | A * | 2/1991 | Aitcheson et al. ............ 264/4.6 |
| 5,141,609 | A | 8/1992 | Sweedler et al. |
| 5,148,502 | A | 9/1992 | Tsujiuchi et al. |
| 5,190,666 | A | 3/1993 | Bisconte |
| 5,281,517 | A | 1/1994 | Bacus et al. |
| 5,308,990 | A | 5/1994 | Takahashi et al. |
| 5,312,535 | A | 5/1994 | Waska et al. |
| 5,321,501 | A | 6/1994 | Swanson et al. |
| 5,402,460 | A | 3/1995 | Johnson |
| 5,668,887 | A | 9/1997 | Parker et al. |
| 5,680,484 | A | 10/1997 | Ohyama et al. |
| 5,710,429 | A | 1/1998 | Alfano et al. |
| 5,741,411 | A | 4/1998 | Yeung et al. |
| 5,760,901 | A | 6/1998 | Hill |
| 5,760,951 | A | 6/1998 | Dixon et al. |
| 5,828,408 | A | 10/1998 | Mottin et al. |
| 5,848,123 | A | 12/1998 | Strommer |
| 5,878,103 | A | 3/1999 | Sauer et al. |
| 5,880,838 | A | 3/1999 | Marx et al. |
| 5,885,430 | A | 3/1999 | Kernan |
| 5,909,476 | A | 6/1999 | Cheng et al. |
| 5,915,048 | A | 6/1999 | Hill et al. |
| 5,987,158 | A | 11/1999 | Meyer |
| 6,005,617 | A | 12/1999 | Shimamoto et al. |
| 6,026,174 | A | 2/2000 | Palcic |
| 6,038,067 | A | 3/2000 | George |
| 6,047,080 | A | 4/2000 | Chen et al. |
| 6,072,624 | A | 6/2000 | Dixon et al. |
| 6,091,983 | A | 7/2000 | Alfano et al. |
| 6,130,958 | A | 10/2000 | Rohler et al. |
| 6,165,734 | A | 12/2000 | Garini |
| 6,201,628 | B1 | 3/2001 | Basiji |
| 6,211,955 | B1 | 4/2001 | Basiji |
| 6,215,587 | B1 | 4/2001 | Alfano et al. |
| 6,248,988 | B1 | 6/2001 | Krantz |
| 6,249,341 | B1 | 6/2001 | Basiji |
| 6,251,586 | B1 | 6/2001 | Mulshine |
| 6,251,615 | B1 | 6/2001 | Oberhardt |
| 6,252,979 | B1 | 6/2001 | Lee |
| 6,312,914 | B1 | 11/2001 | Kardos et al. |
| 6,388,809 | B1 | 5/2002 | MacAulay |
| 6,452,179 | B1 | 9/2002 | Coates et al. |
| 6,529,614 | B1 | 3/2003 | Chao et al. |
| 2001/0012069 | A1 | 8/2001 | Derndinger et al. |
| 2002/0161534 | A1 | 10/2002 | Adler et al. |

OTHER PUBLICATIONS

Kikuchi, S. et al., "Three-dimensional microscopic computed tomography based on general Radon transform for optical imaging systems," Optics Communications 123 (1996).

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-382, 1987.

Gilbert, P, "Iterative Methods for the Three dimensional Reconstruction of an Object from Projections," Journal of Theoretical Biology 36pp. 105-117, 1972.

Oppenheim, BE, More Accurate Algorithms for Iterative 3 dimensional Reconstruction, IEEE Transactions on Nuclear Science NS-21pp. 72-77, 1974.

Singer, JR, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32pp. 205-216, 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947-1957,1989, #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-193, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, 3$^{rd}$ ed., Wiley-Liss, 1995.

HJ Tiziani and MI Uhde, Three-dimensional analysis by a microlens array confocal arrangements (*Applied Optics* 33, 567 [1994]).

Bayat, S, Le Duc, G, Porra, L, Berrruyer, G, Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney, JH and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," Science, vol. 296, pp. 541-545, Apr. 19, 2002.

Sharpe, J, review, "Optical Projection Tomography as a New Tool for Studying Embryo Anatomy," *J. Anat.* (2003), pp. 175-181.

RH Anderson, "Close-up imaging of documents and displays with lens arrays," *Applied Optics* 18, 477 (1979).

Kak, A.C. and Slaney, M.,*Principles of Computerized Tomographic Imaging*, IEEE Press, New York, 1988.

E.G. Steward, *Fourier Optics: An Introduction*, 2nd ed. (Halsted Press, New York, 1987).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements," Cytometry, vol. 2, No. 5, pp. 327-336 (1982).

M. Rozycka, et al., "Optical Diffraction as a Tool for Semiautomatic, Quantitative Analysis of Tissue Specimens," Cytometry, vol. 2, No. 4, pp. 244-248 (1982).

W.H. Press et al., *Numerical Recipes in C* (New York: Cambridge University Press, 1988).

Almeida and Fuji, Fourier transform differences and averaged simularities in diatoms, Applied Optics, vol. 18, No. 10, pp. 1663-1667, (1979).

Smolinska and Dawidowicz, "Extraction of common or different part from optical images," Institute of Physics, Warsaw Technical University, 222-223. (Undated).

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149-156, 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78:435-449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504-509.

George, JS et al., "Virtual Pinhole Confocal Microscope," Physics Division Progress Report, www.lanl.gov/p/pdfs/papp_pinhole.pdf, (1999-2000).

Pawley, JB, *Handbook of Biological Confocal Microscopy*, Plenum Press, NY, 479-490 (1995).

Schmitz, "Perfomance Characteristics of a Silicon Photodiode (SiPD) Based Instrucment for Fast Functional Optical Tomography," undated, SUNY Downstate Medicinal Center Brooklyn, NY.

Schmitz, "Instrumentation for Real-Time Dynamic Optical Tomography," undated, SUNY Downstate Medicial Center Brooklyn, NY.

Lee and Nelson, "Stanley F. Patten, Jr., M.D., Ph.D. and the Development of an Automated Papanicolaou Smear Screening System," Cancer, vol. 81, No. 6 , pp. 332-336. (Undated).

* cited by examiner

AUTOMATED CELL SAMPLE ENRICHMENT PREPARATION METHOD

RELATED APPLICATION

This application claims priority from and is a continuation-in-part of co-pending U.S. application Ser. No. 10/984,221 of Nelson et al., filed Nov. 9, 2004, entitled "AUTOMATED CELL PREPARATION SYSTEM AND METHOD," that is hereby incorporated by reference.

FIELD OF THE INVENTION

The present invention relates to biological cell sample enrichment preparation in general, and, more particularly, to a system and method for automated cell sample enrichment for biological cells in liquid suspension.

BACKGROUND OF THE INVENTION

Specimen preparation for biological cells, for example, in cancer cell analysis using cytology or flow cytometry, has typically consisted of preparing specimens on microscope slides or suspending specimens in a fluid medium. One example of a cell separator is disclosed in U.S. Pat. No. 4,755,287, issued Jul. 5, 1988 to Jones, entitled "FIVE STAGE INTERNAL CELL SEPARATOR." Jones discloses a simple cell separator that permits separation on the basis of size.

Unfortunately known methods require an undue amount of handling for additional processing, such as staining prior to optical analysis. The specimen must be removed from the cell separator for further processing in separate devices or systems. Thus, known methods do not provide an enriched cell sample in the form of a concentrated suspension where the cells are stained and prepared for subsequent analysis in an optical system while promoting ease of handling with an acceptable throughput.

Now for the first time, the present invention provides a cell sample enrichment preparation method that provides an integrated system for producing an enriched cell sample, stained and packed in a cassette that promotes ease of handling for subsequent analysis in an optical system. One example of an automated three-dimensional microscopy system that would benefit from the present invention is disclosed by Nelson in U.S. Pat. No. 6,522,775 issued Feb. 18, 2003, entitled "Apparatus and Method for Imaging Small Objects in a Flow Stream Using Optical Tomography," the contents of which are incorporated by reference.

SUMMARY OF THE INVENTION

The present invention provides a method for automated cell sample enrichment preparation where biological cells are injected into a first subchamber and flowed through the first subchamber, through a large pore filter and into a second subchamber so that the large pore filter retains large particles in the first subchamber, while the biological cells pass through the first filter into the second subchamber and are retained by a small pore filter. After clearing, the biological cells are stained. A solvent exchange leaves the biological cells in solvent and they are released into a concentration module where a portion of the solvent is removed to form an enriched concentrated cell suspension.

DETAILED DESCRIPTION OF THE PREFERRED EMBODIMENT

The invention is described herein with respect to specific examples relating to biological cells, however, it will be understood that these examples are for the purpose of illustrating the principals of the invention, and that the invention is not so limited.

Figure 1:
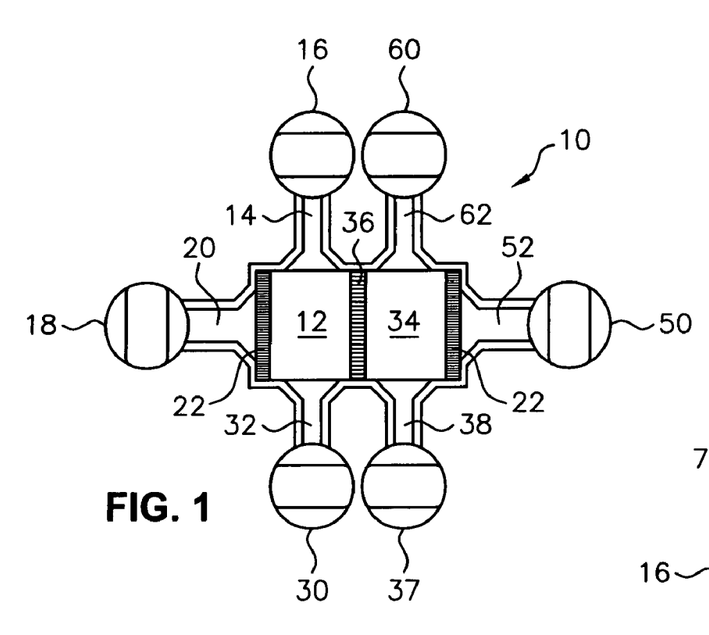
FIG. 1 schematically shows an example illustration of a system and method for automated cell sample enrichment preparation as contemplated by an embodiment of the present invention.

Referring now to FIG. 1, an example of a system for automated cell sample enrichment as contemplated by an embodiment of the present invention is shown including a chamber 10, where the chamber 10 has an interior separated into first and second subchambers 12, 34 respectively by a large pore filter 36. Each of the subchambers 12, 34 is juxtaposed between the large pore filter 36 at one end and one of two small pore filters 22 at an opposing end. The large pore filter and small pore filters may advantageously be sized and/or fitted to form a seal around the inner wall of the chamber 10. O-rings or the like may be used to mechanically seal the filters against the inner wall of the chamber 10. The chamber 10 may be of any suitable shape for enclosing a volume such as, for example, cylindrical, cubical or equivalents.

To allow the introduction of specimens and processing fluids or other mixtures as desired, the chamber 10 further advantageously includes a plurality of valves and ports. A first port 14 allows specimen sample, fluids, fluid mixtures and the like to enter the first subchamber 12 as controlled by a first valve 16. A second valve 18 is coupled at a second port 20 and separated from the first subchamber 12 by the first small pore filter 22. A third valve 30 is coupled at a third port 32 directly to the first subchamber 12. The second subchamber 34 is coupled to a fourth valve 37 at a fourth port 38. A fifth valve 50 is coupled a fifth port 52 that is separated from the second subchamber 34 by one of the small pore filters 22. A sixth valve 60 is coupled to the second subchamber 34 by a sixth port 62. As described in detail hereinbelow, the first through sixth valves operate cooperatively to allow separation of large particles from biological cells.

In one example embodiment, a first small pore filter 22, and a second small pore filter 22 are sized to retain particles as small as biological cells. The small pore filters may advantageously be filters having a filter pore size in the range of about 8 microns to 10 microns. Such small pore filters are commercially available as, for example, nucleopore polycarbonate filters and equivalents. The large pore filter 36 has filter pores sized to retain particles larger than biological cells, herein generally referred to as "large particles." The large pore filter may advantageously be a filter having a filter pore size greater than 10 microns, and, more preferably, in the range of about 100 microns to 105 microns. Such large pore filters are commercially available as, for example, nylon monofilament, polypropylene monofilament filters and equivalents. Note that as used herein the term "pore size" refers to the size of filter holes and is intended to also mean a filter screen size. While terms such as "pore filter" are used herein by way of example, the invention is not so limited and equivalent filters are also intended to be included whether manufactured with pores or mesh type screen constructions.

The enrichment method of the invention enriches biological specimens for use in subsequent analysis by eliminating large particles including objects, tissue, clumps or groups of cells that are too large to qualify as objects or cells of interest requiring analysis. The resulting enriched sample may then be stained and concentrated in a single system to allow more efficient analysis by automated or manual optical tomography or microscopy methods. Due to the filtering and concentration of the cell sample the enriched sample may be more likely to contain cells that may be diagnostic of cancer. Such cells may include preinvasive cancer cells, or invasive cancer cells as may be harvested for screening a patient for cancer or determining whether a patient will develop invasive cancer. The cell enrichment sample preparation of the present invention may be used to enrich cell samples for later analysis of various diseases such as lung cancer, throat cancer, cervical cancer, ovarian cancer, breast cancer, prostate cancer, skin cancer, cancer of the gastrointestinal tract, lymphatic cancer and bone cancer. The specific size of cancer cells has been well documented and is known to those skilled in the art and need not be further detailed here. See, for Example, Lee and Nelson, "Stanley F. Patten, Jr., M.D., Ph.D. and the Development of an Automated Papanicolaou Smear Screening System," CANCER, Vol. 81, No. 6, pp. 332-336 (a copy of which is appended hereto). Patten's Table 1a is a comprehensive morphological criteria list for different cervical cells measured in microns squared and pixels. The table includes various types of cells including cancer cells at varying stages, including cancinoma in situ (also known as preinvasive). It is well known that cell sizes vary with tissue types, but not organs, thus the measurements are applicable to other organs in the body such as the throat and lungs.

Figure 2:
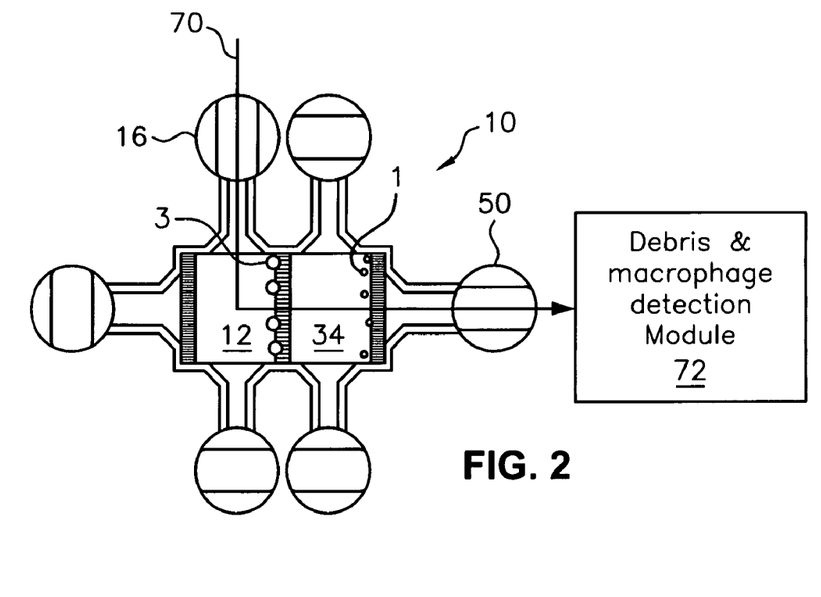
FIG. 2 schematically shows the example illustration of the system and method for automated cell sample enrichment preparation in operation as contemplated by an embodiment of the present invention.

Referring now to FIG. 2, the system for automated cell sample enrichment preparation of FIG. 1 is shown in operation as contemplated by an embodiment of the present invention. As indicated by directional arrow 70 a biological cell sample, including large particles 3 and biological cells 1, is injected into the first subchamber 12 by opening the first valve 16 and allowing the sample to flow into the first subchamber 12. When the fifth valve 50 is opened at the same time as the first valve 16 (the other valves remaining closed) the specimen flows through the first subchamber into the second subchamber filtered by the large pore filter 36. The flow through the chambers continues until the large particles 3 are retained by the large pore filter, while smaller objects of interest 1, such as biological cells, pass through the large pore filter and into the second subchamber where they are retained by the second small pore filter. Fluid from the second subchamber 34, along with debris smaller than the small pore filter size pass, through the second small pore filter. If desired, the fluid and debris may be routed to an optional debris and macrophage detection module 72 for analysis.

Figure 3:
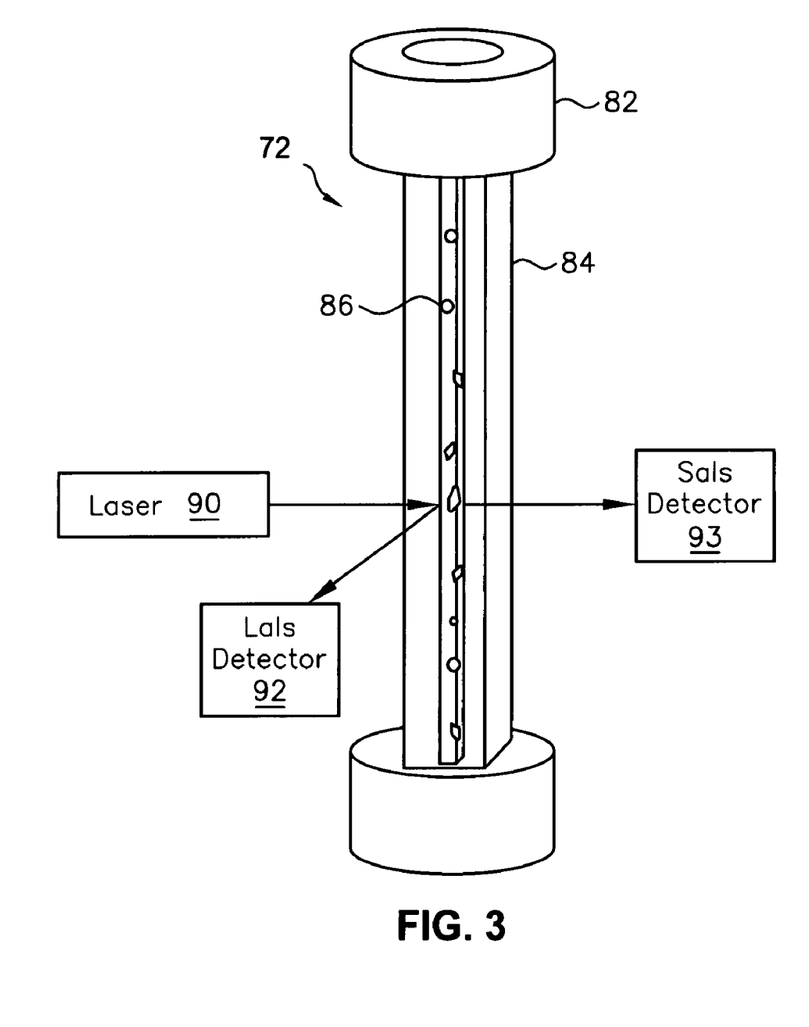
FIG. 3 schematically shows an example illustration of a detection module for optional use with automated cell sample enrichment preparation as contemplated by an embodiment of the present invention.

Referring now to FIG. 3, an example illustration of a detection module for optional use with automated cell concentration preparation as contemplated by an embodiment of the present invention is schematically shown. The optional debris and macrophage detection module 72 advantageously includes a set of automatic exchange interconnects 82 attached at opposing ends of a capillary tube 84. Particles of debris 86 flow through the capillary tube 84. A laser diode 90 is positioned for illuminating particles in the capillary tube 84 so as to produce small angle light scattering (SALS) for particle size detection and large angle light scattering (LALS) for particle nuclear complexity detection. A plurality of silicone photodiode detectors 92, 93 may advantageously be positioned to receive scattered light including small angle light scattering for particle size detection and large angle light scattering for particle nuclear complexity detection. In one useful embodiment, the capillary tube 84 comprises circular or rectangular fused silica capillary tubing.

Figure 4A:
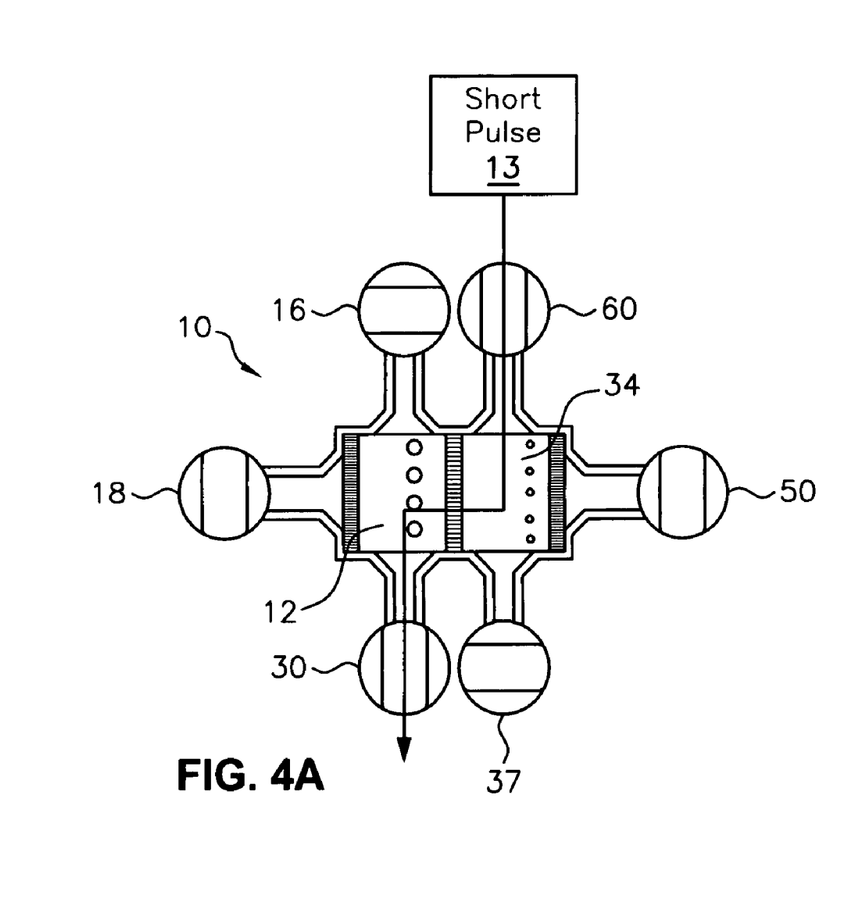
FIGS. 4A and 4B schematically show example illustrations of a system for automated cell sample enrichment preparation in operation to clear unwanted large particles as contemplated by an embodiment of the present invention.

Referring now to FIG. 4A an example illustration of a system for automated cell concentration preparation in operation to clear retained large particles as contemplated by an embodiment of the present invention is schematically shown. The cell concentration preparation system is configured to free large particles retained against the large pore filter by back flushing through the large pore filter using a clearing fluid. The third valve 30 and sixth valve 60 are opened to allow back flushing by injecting a pulse of clearing fluid 13 into the second subchamber 34 and back through the large pore filter. During the back flushing the smaller objects of interest 1 will remain proximate the second small pore filter 22. One useful clearing fluid includes a reagent of 50% ethanol ($C_2H_5OH$).

Figure 4B:
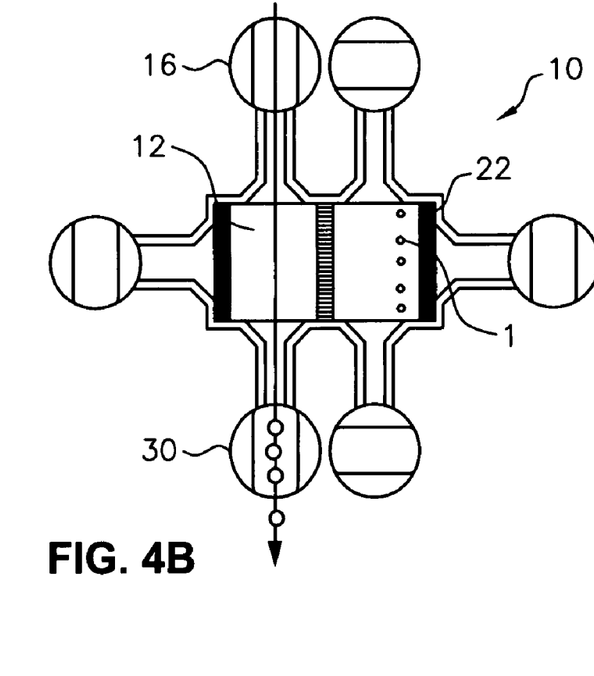

Referring now to FIG. 4B, an example illustration of a system for automated cell sample enrichment preparation in operation to clear large particles as contemplated by an embodiment of the present invention is schematically shown. Large particles freed from the large pore filter by back flushing, as described above with reference to FIG. 4A, are removed from the first subchamber 12 by injecting a clearing fluid through the first subchamber 12 along a flow path through the first valve 16 and third valve 30 using clearing fluid. As above, one useful clearing fluid includes a reagent of 50% ethanol. Once the large particles are removed from the chamber 10, the biological cells retained by the small pore filters may be further processed to prepare an enriched cell sample.

Figure 5:
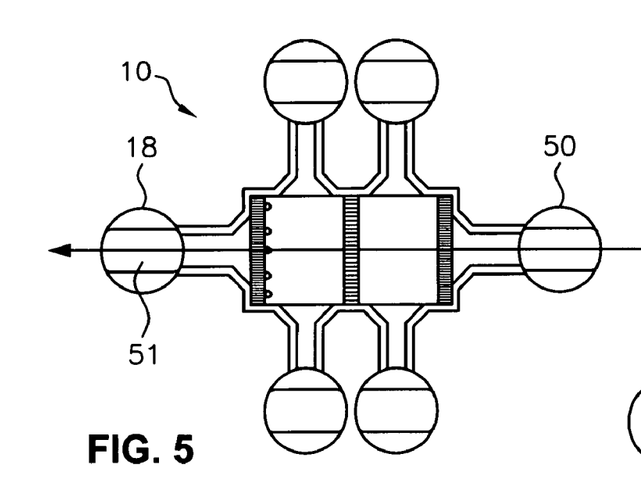
FIG. 5 schematically shows an example illustration of a system for automated cell sample enrichment preparation in operation for staining as contemplated by an embodiment of the present invention.

Referring now to FIG. 5 an example illustration of a system for automated cell sample enrichment preparation in operation for staining as contemplated by an embodiment of the present invention is schematically shown. As an example of one possible staining process, staining proceeds along the following steps:

Stain step 1: the cells are pre-stained twice, and rinsed once with a reagent comprising 50% ethanol, where the flow 51 is in a first direction following a path through the second small pore filter, through the second subchamber, through the large pore filter, into and through the first subchamber and out of the chamber 10 through the first small pore filter.

Stain step 2: the cells are pre-stained twice, and rinsed twice with a reagent comprising double distilled (DD) water ($H_2O$), where the flow is in a second direction that is the reverse of the first direction. Due to reversing the flow, the cells are retained in the chamber 10 by the second small pore filter.

Stain step 3: the cells are pre-stained once, and rinsed 3 times with a reagent comprising $DDH_2O$, where the flow is in the first direction.

Stain step 4: a timed stain of 1 minute is carried out with a reagent/stain comprising Hematoxylin, where the flow is in the second direction.

Stain step 5: a single post-stain and a single rinse with a reagent comprising $DDH_2O$, is carried out where the flow is in the first direction.

Stain step 6: a single post-stain and double rinse with a reagent comprising $DDH_2O$+4% (by volume) ammonia, is carried out where the flow is in the second direction.

Stain step 7: the cells undergo a single post-stain and a triple rinse with a reagent comprising $DDH_2O$, where the flow is in the first direction, thus completing one rinsing and staining procedure. Additional protocols for counterstains, antibody based probes, and so on can be added and implemented analogous to stain steps 4 thru 7 with appropriate reagents and steps adapted as required and understood by those skilled in the art having the benefit of this disclosure.

Still referring to FIG. 5, the staining procedure may be followed by a solvent exchange procedure. As in the staining procedure described above, the flow of solvent through the chamber 10 alternates by reversing directions through the chamber and filters. One example of the solvent exchange procedure includes the steps of:

Solvent exchange step 1: solvent is exchanged with solvent comprising 50% ethanol ($C_2H_5OH$). Cells are then allowed to equilibrate by transmembrane diffusion.

Solvent exchange step 2: solvent is exchanged with solvent comprising 80% ethanol. Cells are then allowed to equilibrate by transmembrane diffusion.

Solvent exchange step 3: solvent is exchanged with solvent comprising 100% ethanol. Cells are then allowed to equilibrate by transmembrane diffusion.

Solvent exchange step 4: solvent is again exchanged with solvent comprising 100% ethanol. Cells are then allowed to equilibrate by transmembrane diffusion. The second rinse is a factor of safety for full cellular dehydration, and for competing the ethanol exchange.

Solvent exchange step 5: solvent is exchanged with solvent comprising 50% ethanol and 50% xylene. Cells are then allowed to equilibrate by transmembrane diffusion.

Solvent exchange step 6: solvent is again exchanged with solvent comprising 50% ethanol and 50% xylene to insure transition. Cells are then allowed to equilibrate by transmembrane diffusion.

Solvent exchange step 7: solvent is exchanged with solvent comprising 100% xylene. Cells are then allowed to equilibrate by transmembrane diffusion.

Solvent exchange step 8: solvent is exchanged with solvent comprising 100% xylene. Cells are then allowed to equilibrate by transmembrane diffusion.

Solvent exchange step 9: solvent is exchanged for a third rinse/exchange with solvent comprising 100% xylene. Cells are then allowed to equilibrate by transmembrane diffusion.

Solvent exchange step 10: prior to releasing cells for transfer, solvent is exchanged with a solvent comprising 100% xylene while pulsing in the second direction, and completing solvent exchange to xylene. After this step, a mixture of xylene and dehydrated cells remain in the second subchamber 34.

Figure 6:
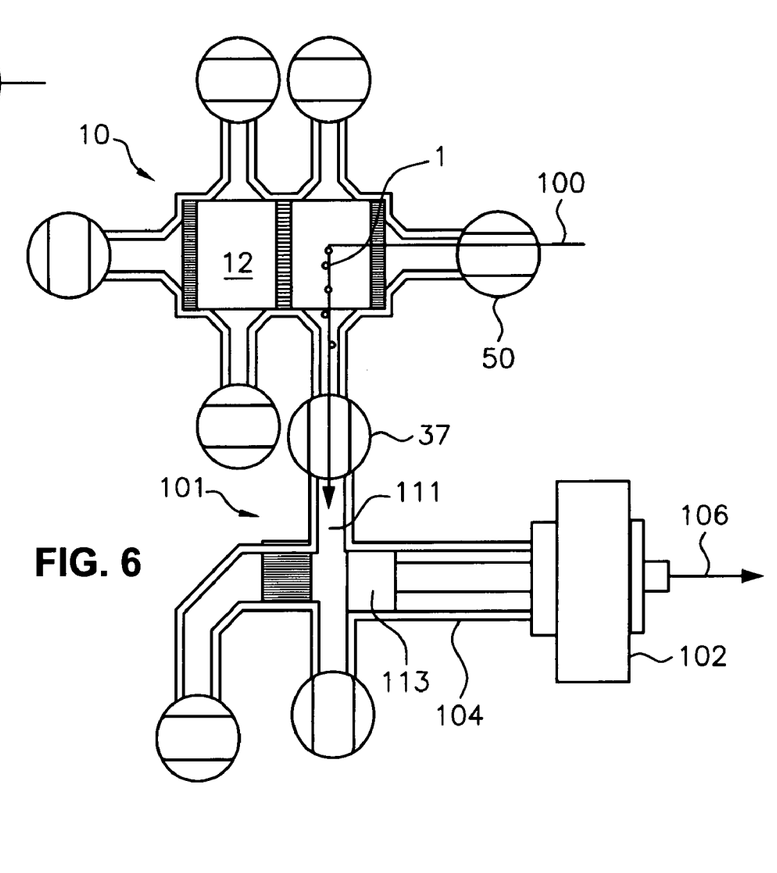
FIG. 6 schematically shows an example illustration of a system for automated cell sample enrichment preparation in operation to release cells for transfer to a concentration module as contemplated by an embodiment of the present invention.

Referring now to FIG. 6, an example illustration of a system for automated cell sample enrichment preparation in operation to release cells for transfer as contemplated by an embodiment of the present invention is schematically shown including a cell concentration module. A cell concentration module 101 includes a syringe pump 102 and a passage 111 coupled to the output of the fourth valve 37 through an input leg 104. Following the staining and solvent exchange processes, cells 1, now dehydrated by the stain and solvent processing described above, are transferred to the cell concentration module 101 by aspirating the syringe pump 102 as indicated by directional arrow 100. The syringe pump 102 is aspirated (plunger 113 is withdrawn) as indicated by directional arrow 106 while providing positive bias pressure to draw in the cells.

Figure 7:
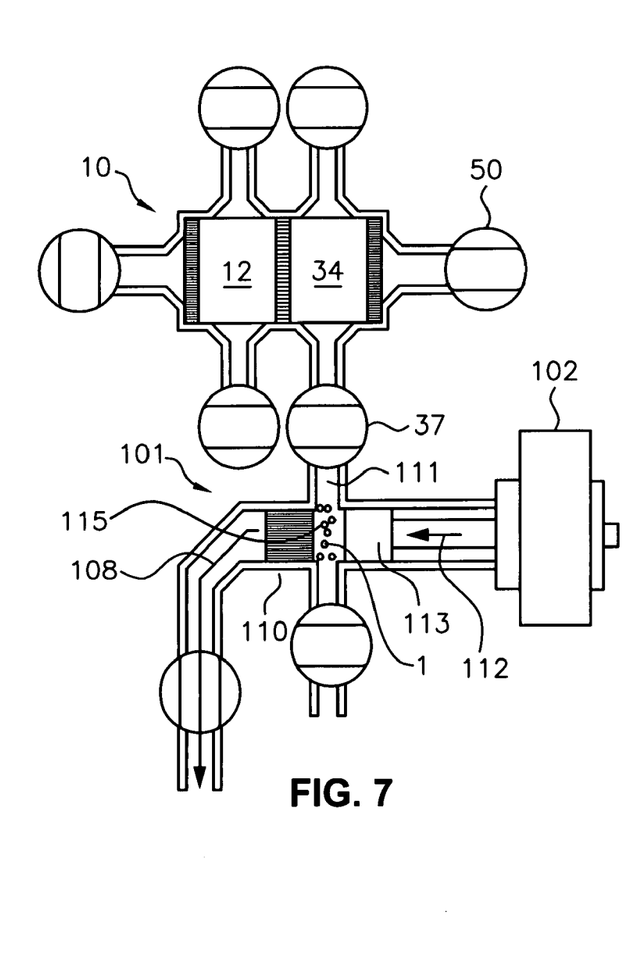
FIG. 7 schematically shows an example illustration of a system for automated cell sample enrichment preparation in operation to concentrate a cell slurry in preparation for transfer as contemplated by an embodiment of the present invention.

Referring now to FIG. 7, an example illustration of a system for automated cell sample enrichment preparation in operation to concentrate a cell suspension in preparation for transfer as contemplated by an embodiment of the present invention is schematically shown. In this configuration the fourth valve 37 is closed after the cells 1 have been transferred to passage 111 so that the cells are captured in passage 111. A conduit 108 is connected through a filter 110 to passage 111. Filter 110 is selected to have a pore size at least as small as the small pore filters, that is, small enough to pass the xylene solvent, but large enough to retain the cells 1. By dispensing cell pre-concentration module syringe pump 102 by moving the plunger forward as indicated by directional arrow 112, a portion of the xylene solvent is forced through the filter 110 and an enriched concentrated cell suspension 115 remains in passage 111.

Figure 8:
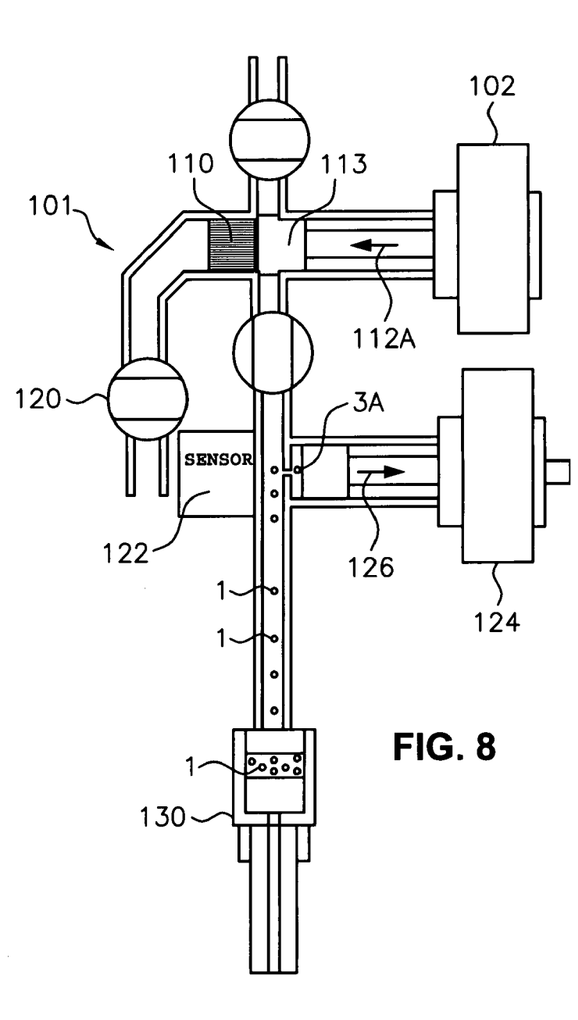
FIG. 8 schematically shows an example illustration of a system for automated cell sample enrichment preparation in operation to optionally reject particles of no interest as contemplated by an embodiment of the present invention.

Referring now to FIG. 8, an example illustration of a system for automated cell sample enrichment preparation in operation to optionally analyze and selectively remove cells of no interest while sending cells of interest to a sample transport device as contemplated by an embodiment of the present invention is schematically shown. In order to dispense the enriched concentrated cell suspension 115, the cells are allowed to flow down towards a capillary receptacle 130. Using a slow flow, as by gravity or other flow device, cells may optionally be allowed to flow past an optional detection module 122. Optional detection module 122 may be, for example, a known optical detection module or equivalent. When passing cells or other particles of no interest 3A are detected by the optional detection module 122, the flow of particles is slowed so that they can be aspirated by a second syringe pump 124 as indicated by directional arrow 126 for later disposal. The remaining cells continue to flow to the capillary receptacle 130.

Before processing another sample, all upstream fluidics receive a precision cleaning protocol. All filters receive multiple backwashes and all lines are fully deproteinated in accordance with standard practices. In an alternate embodiment, the chamber 10 may be made from disposable materials and discarded after each use. In the case of a disposable chamber, precision cleaning of the chamber is not needed since a new chamber is used for each new sample. Use of a disposable chamber avoids cross-contamination of samples.

Figure 9:
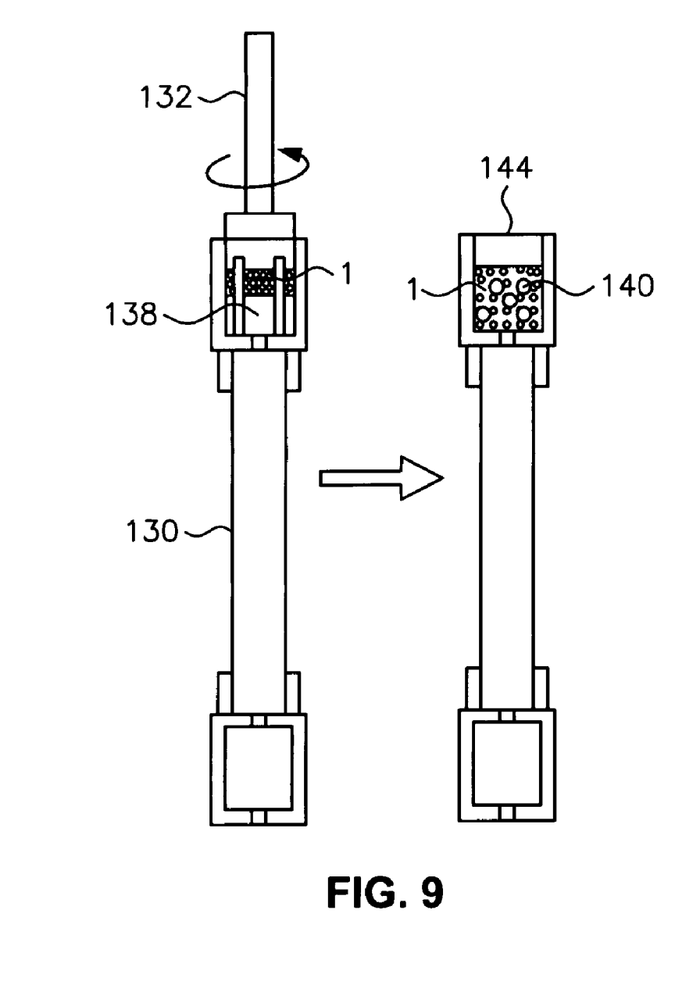
FIG. 9 schematically shows an example illustration of a capillary receptacle for use in automated cell sample enrichment preparation as contemplated by an embodiment of the present invention.

Referring now to FIG. 9, an example illustration of a capillary receptacle for use in automated cell sample enrichment preparation as contemplated by an embodiment of the present invention is schematically shown. Any remaining xylene is removed from the enriched concentrated cell suspension 115 by evaporation with vacuum to create a cell layer for subsequent blending. In a vacuum, the cells 1 are blended in the capillary receptacle 130 with an optical gel 138, creating many vacuoles and pockets 140. A mixer 132 may preferably comprise a single use molded plastic component that is discarded when operation is complete. The optical gel 138 may be selected using conventional optical design principles. The optical gel preferably has an index of refraction selected to optimize light transmission. The optical gel 138 should preferably have an index of refraction that matches the material of the capillary receptacle. Ready-to-use thixotropic optical gels having suitable clarity and refraction indices are commercially available from companies such as Nye Optical Products of Fairhaven, Mass., USA.

Figure 10:
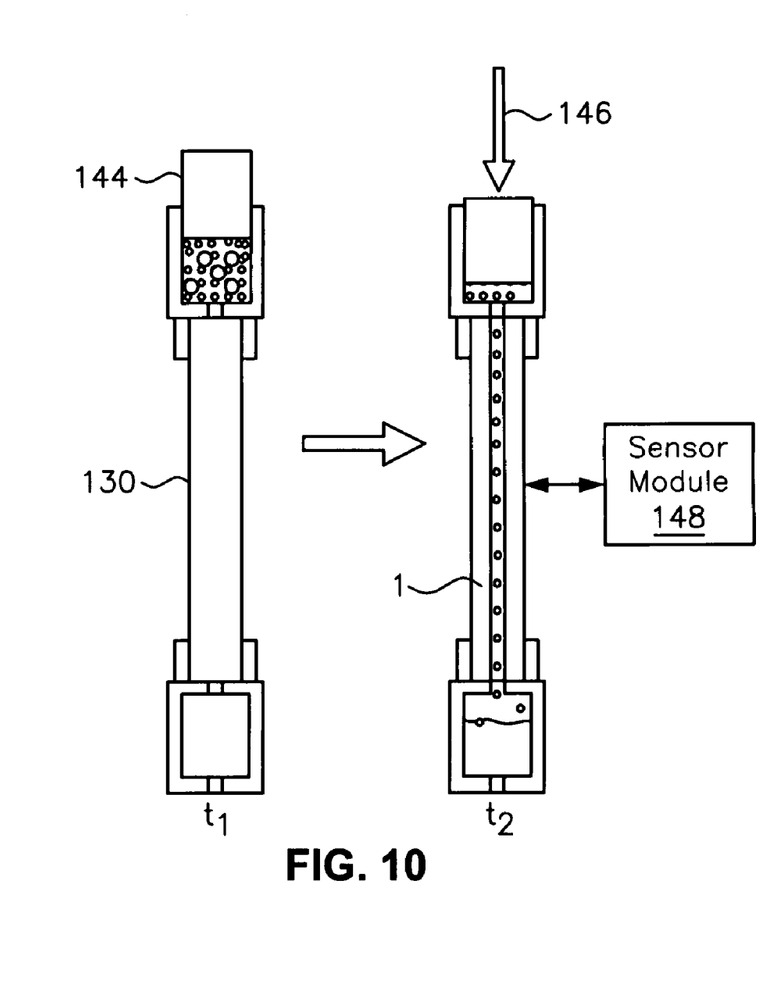
FIG. 10 schematically shows an example illustration of a capillary receptacle and sensor module for use in automated cell sample enrichment preparation as contemplated by an embodiment of the present invention.

Referring now to FIG. 10, an example illustration of a capillary receptacle and sensor module for use in automated cell sample preparation as contemplated by an embodiment of the present invention is schematically shown. At time $t_1$, while maintained in a vacuum, a disposable piston/cap 144 is placed in the capillary receptacle now containing cells embedded in optical gel. At time $t_2$, force 146 is applied and sensor module 148 is used to verify proper mean load spacing of the cells 1 in optical gel. Sensor module 148 may comprise a known automated visioning system, microscope or equivalents.

Figure 11:
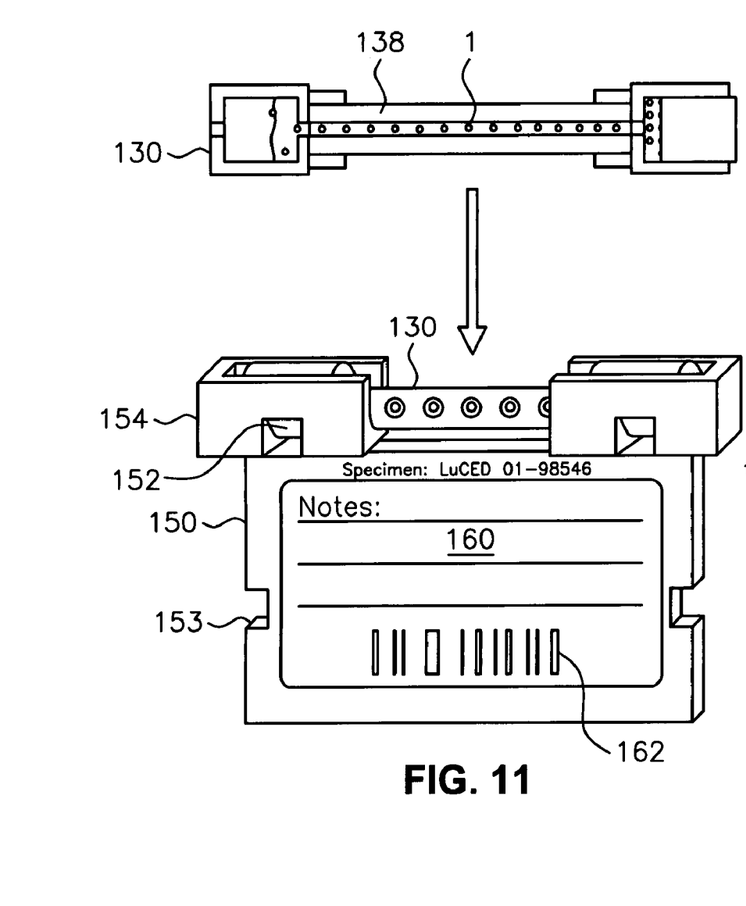
FIG. 11 schematically shows an example illustration of a capillary receptacle placed into a cassette for use in automated cell sample enrichment preparation as contemplated by an embodiment of the present invention.

Referring now to FIG. 11, an example illustration of a capillary receptacle placed into a cassette for use in automated cell sample enrichment preparation as contemplated by an embodiment of the present invention is schematically shown. The capillary receptacle 130 is placed in a protective handling cassette 150. The protective handling cassette 150 includes access points 152 for robotic extraction of the capillary receptacle 130, registry points 153 for automatic alignment verification and grip points 154 for cassette manipulation. The protective handling cassette 150 may also advantageously include identifying indicia 160 including, for example, a bar code 162. The protective handling cassette 150 may have a generally rectangular shape so as to allow stacking with one or more additional handling cassettes.

Figure 12:
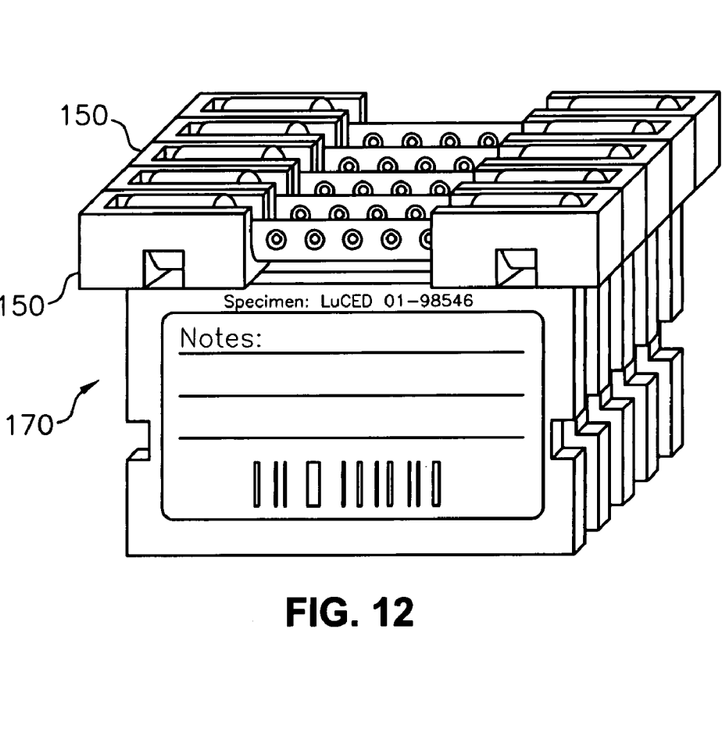
FIG. 12 schematically shows an example illustration of cassettes in stackable queues for use in automated cell sample enrichment preparation as contemplated by an embodiment of the present invention.

Referring now to FIG. 12, an example illustration of cassettes in stackable queues for use in automated cell analysis as contemplated by an embodiment of the present invention is schematically shown. Cassettes 150 are placed in stackable queues 170 that buffer the input of the (not shown) 3D microscopy reader. Cassette queues are also removable for reading.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for automated cell enrichment preparation using a chamber having opposing ends, where each opposing end is covered by one of a first small pore filter and a second small pore filter, a large pore filter is mounted between the opposing ends to divide the chamber into a first subchamber and a second subchamber, wherein the large pore filter has a pore size large enough to pass biological cells and the small pore filters have a pore size small enough to retain biological cells, the method comprising the steps of:

injecting a biological cell sample including large particles and biological cells into the first subchamber;

creating a flow of the biological cell sample through the first subchamber, through the large pore filter and into the second subchamber so that the biological cells pass through the large pore filter into the second subchamber and are retained by the second small pore filter, and the large particles are retained by the large pore filter;

using a short impulse back through the second subchamber, large pore filter and into the first subchamber to dislodge the large particles from the large pore filter;

removing the large particles from the first subchamber, while the biological cells remain retained by the second small pore filter in the second subchamber;

staining the biological cells by alternately injecting a stain followed by a rinse through the first subchamber and the second subchamber;

exchanging solvent in the first subchamber and the second subchamber, allowing the biological cells to equilibrate after each exchange until the solvent exchange is complete;

coupling the chamber to a concentration module and releasing the biological cells and solvent from the chamber into the concentration module;

removing solvent from the concentration module to form an enriched concentrated cell suspension;

transferring the enriched concentrated cell suspension into a capillary receptacle coupled to receive the enriched concentrated cell suspension from the concentration module; and blending the enriched concentrated cell suspension in the capillary receptacle with an optical fluid having an index of refraction selected for improving light transmission through the capillary receptacle.

2. The method of claim 1 wherein the small pore filters have a filter pore size in the range of 8 microns to 10 microns.

3. The method of claim 2 wherein the first small pore filter and the second small pore filter comprise nucleopore polycarbonate filters.

4. The method of claim 1 wherein the large pore filter has a filter pore size in the range of 100 microns to 105 microns.

5. The method of claim 4 wherein the large pore filter comprises a filter selected from the group consisting of a nylon monofilament filter and a polypropylene monofilament filter.

6. The method of claim 1 further comprising the steps of uncoupling the capillary receptacle, and capping and mounting the capillary receptacle in a cassette.

7. The method of claim 6 wherein the capillary receptacle comprises:
- a cassette housing having a capillary gripper;
- a pair of opposing clips on the top for releasably holding a capillary receptacle;
- a plurality of access points for robotic extraction of the capillary receptacle;
- a plurality of registration points for automatic alignment verification; and
- a plurality of grip points for cassette manipulation.

8. The method of claim 1 wherein each of the small pore filters retain biological cells having a width greater than 10 microns.

9. The method of claim 1 wherein the large pore filter retains large particles having a width greater than 100 microns.

10. The method of claim 1 wherein the capillary receptacle comprises circular or rectangular fused silica capillary tubing.

11. The method of claim 1 wherein the chamber is disposable.

12. The method of claim 1 wherein the optical fluid is an optical gel.

13. The method of claim 12 wherein the optical gel is a thixotropic gel.

14. The method of claim 12 wherein the optical gel has an index of refraction that matches the material of the capillary receptacle.

* * * * *